United States Patent
Sakashita

(10) Patent No.: US 12,141,969 B2
(45) Date of Patent: Nov. 12, 2024

(54) MEDICAL IMAGE PROCESSING DEVICE AND MEDICAL IMAGE PROCESSING PROGRAM

(71) Applicant: NIDEK CO., LTD., Gamagori (JP)

(72) Inventor: Yusuke Sakashita, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 153 days.

(21) Appl. No.: 17/621,301

(22) PCT Filed: Jul. 29, 2020

(86) PCT No.: PCT/JP2020/028976
§ 371 (c)(1),
(2) Date: Dec. 21, 2021

(87) PCT Pub. No.: WO2021/020419
PCT Pub. Date: Feb. 4, 2021

(65) Prior Publication Data
US 2022/0358640 A1     Nov. 10, 2022

(30) Foreign Application Priority Data

Jul. 29, 2019    (JP) .................................. 2019-138931

(51) Int. Cl.
*G06T 7/00*      (2017.01)
*A61B 3/00*      (2006.01)
(Continued)

(52) U.S. Cl.
CPC .......... *G06T 7/0012* (2013.01); *A61B 3/0025* (2013.01); *G06T 11/00* (2013.01);
(Continued)

(58) Field of Classification Search
CPC .................. G06T 7/0012; G06T 11/00; G06T 2207/30096; G06T 2210/41;
(Continued)

(56) References Cited

U.S. PATENT DOCUMENTS

2011/0190657 A1* 8/2011 Zhou ................... G16H 50/70
                                                            600/558
2012/0050308 A1* 3/2012 Nakano .................. G06T 5/50
                                                             345/592

(Continued)

FOREIGN PATENT DOCUMENTS

JP          2006149654 A  *  6/2006
JP          2010-097475 A     4/2010
(Continued)

OTHER PUBLICATIONS

JP2018121886A (Machine Translation on Mar. 25, 2024) (Year: 2018).*

(Continued)

*Primary Examiner* — Michael Le
(74) *Attorney, Agent, or Firm* — Oliff PLC

(57) ABSTRACT

A controller of a medical image processing device acquires a medical image of a subject. The controller causes a display to display a pre-modification image in which at least the position or range of a lesion to be modified on the medical image is displayed. The controller receives an instruction to designate at least the position or range of the lesion to be modified in a state in which the pre-modification image is displayed on the display. When at least the position or range of the lesion is designated, the controller acquires a predicted disease image in which the lesion is modified according to the designated information on the basis of the medical image. The controller causes the display to display the predicted disease image and the pre-modification image simultaneously or in a switching manner.

9 Claims, 4 Drawing Sheets

(51) Int. Cl.
  *G06T 11/00* (2006.01)
  *G06V 10/764* (2022.01)
  *G16H 30/40* (2018.01)
(52) U.S. Cl.
  CPC ........... *G06V 10/764* (2022.01); *G16H 30/40* (2018.01); *G06T 2207/30096* (2013.01); *G06T 2210/41* (2013.01)
(58) Field of Classification Search
  CPC . G06T 2207/10081; G06T 2207/10101; G06T 2207/20072; G06T 2207/20076; G06T 2207/20081; G06T 2207/20084; G06T 2207/30024; G06T 2207/30041; A61B 3/0025; G06V 10/764; G06V 10/82; G06V 2201/03; G16H 30/40; G16H 30/20; G16H 50/20; G16H 50/70; G06F 3/0481
  See application file for complete search history.

(56) References Cited

U.S. PATENT DOCUMENTS

| | | | |
|---|---|---|---|
| 2014/0153795 A1* | 6/2014 | Lenox | G06T 7/0012 382/128 |
| 2015/0016705 A1* | 1/2015 | Kubo | A61B 1/043 382/132 |
| 2016/0157803 A1 | 6/2016 | Keller | |
| 2020/0069175 A1 | 3/2020 | Kumagai et al. | |
| 2020/0380675 A1* | 12/2020 | Golden | G06T 7/143 |
| 2021/0030385 A1 | 2/2021 | Keller | |
| 2022/0000351 A1* | 1/2022 | Yamada | G16H 30/40 |

FOREIGN PATENT DOCUMENTS

| | | | | |
|---|---|---|---|---|
| JP | 2013-128694 A | | 7/2013 | |
| JP | 2013-198817 A | | 10/2013 | |
| JP | 2017-537706 A | | 12/2017 | |
| JP | 2018-121885 A | | 8/2018 | |
| JP | 2018121886 A | * | 8/2018 | ........... A61B 3/0025 |
| JP | 2018147387 A | * | 9/2018 | |
| JP | 2019-208852 A | | 12/2019 | |

OTHER PUBLICATIONS

Sep. 29, 2020 International Search Report issued in International Patent Application No. PCT/JP2020/028976.

* cited by examiner

MEDICAL IMAGE PROCESSING DEVICE AND MEDICAL IMAGE PROCESSING PROGRAM

TECHNICAL FIELD

The present disclosure relates to a medical image processing device that processes a medical image that is an image of a tissue of a subject and a medical image processing program executed by the medical image processing device.

BACKGROUND ART

In recent years, various techniques for processing medical images to obtain useful information have been proposed. For example, an image processing device described in Patent Literature 1 acquires a diagnosis result of an eye to be examined for the purpose of obtaining an image analysis result suitable for a disease and processes an image of the eye to be examined using a processing method according to the acquired diagnosis result.

CITATION LIST

Patent Literature

Patent Literature 1: JP 2018-121885 A

SUMMARY OF INVENTION

It is useful for both a doctor and a patient if the doctor can explain, to the patient, the state of a tissue in a case in which a disease occurs, the state of the tissue in a case in which the disease progresses, the state of the tissue in a case in which the disease is cured, and the like while illustrating the subject himself/herself the image of the tissue. However, conventionally, an image of another subject in a state equivalent to the predicted patient state can only be illustrated to the subject at the time of explanation.

A typical object of the present disclosure is to provide a medical image processing device and a medical image processing program that can appropriately present an image useful in explanation from a doctor to a subject.

A medical image processing device provided by a typical embodiment of the present disclosure is a medical image processing device that processes a medical image that is an image of a tissue of a subject. A controller of the medical image processing device executes an image acquisition step of acquiring a medical image of a subject, a pre-modification image display step of displaying, on a display, an image prepared for modification in which at least one of a position and a range of a lesion to be modified on the medical image is displayed, a lesion reception step of receiving an instruction to designate at least one of a position and a range of the lesion to be modified in a state in which the pre-modification image is displayed on the display, a predicted disease image acquisition step of, in a case in which at least one of a position and a range of the lesion is designated, acquiring a predicted disease image in which the lesion is modified according to designated information on the basis of the medical image acquired in the image acquisition step, and a predicted disease image display step of displaying the acquired predicted disease image and the pre-modification image on the display simultaneously or in a switching manner.

A medical image processing program provided by a typical embodiment of the present disclosure is a medical image processing program executed by a medical image processing device that processes a medical image that is an image of a tissue of a subject. The medical image processing program is executed by a controller of the medical image processing device to execute an image acquisition step of acquiring a medical image of a subject, a pre-modification image display step of displaying, on a display, an image prepared for modification in which at least one of a position and a range of a lesion to be modified on the medical image is displayed, a lesion reception step of receiving an instruction to designate at least one of a position and a range of the lesion to be modified in a state in which the pre-modification image is displayed on the display, a predicted disease image acquisition step of, in a case in which at least one of a position and a range of the lesion is designated, acquiring a predicted disease image in which the lesion is modified according to designated information on the basis of the medical image acquired in the image acquisition step, and a predicted disease image display step of displaying the acquired predicted disease image and the pre-modification image on the display simultaneously or in a switching manner.

According to the medical image processing device and the medical image processing program according to the present disclosure, an image useful for explanation from a doctor to a subject is appropriately presented.

The controller of the medical image processing device exemplified in the present disclosure executes an image acquisition step, a pre-modification image display step, a lesion reception step, a predicted disease image acquisition step, and a predicted disease image display step. In the image acquisition step, the controller acquires a medical image of the subject. In the pre-modification image display step, the controller causes the display to display an image prepared for modification in which at least the position or range of the lesion to be modified on the medical image is displayed. In the lesion reception step, the controller receives an instruction to designate at least the position or range of the lesion to be modified in a state in which the pre-modification image is displayed on the display. In the predicted lesion image generation step, when at least the position or range of the lesion is designated, the controller acquires a predicted disease image in which the lesion is modified according to the designated information on the basis of the medical image acquired in the image acquisition step. In the predicted disease image display step, the controller causes the display to display the acquired predicted disease image and the pre-modification image simultaneously or in a switching manner.

According to the medical image processing device exemplified in the present disclosure, when the user inputs an instruction to designate at least the position or range of the lesion to be modified in a state in which the pre-modification image is displayed, the predicted disease image in which the lesion is modified according to the designated information is acquired on the basis of the medical image of the subject. The acquired predicted disease image is then displayed on the display in a state in which the pre-modification image is displayed or in a state of being switched to the pre-modification image. That is, when an instruction to designate a lesion is input, a predicted disease image in which the lesion has been modified on the medical image of the subject is acquired and displayed according to the designated information. Therefore, instead of an image of a subject different from the subject to be explained by the doctor, a predicted disease image in which a medical image of the subject himself who provides explanations is appropriately modified is presented to the subject. Accordingly, an image useful for explanation from the doctor to the subject is appropriately presented to the subject.

In the predicted disease image acquisition step, the controller acquires a predicted disease image based on the medical image of the subject actually photographed. That is, the controller acquires the predicted disease image on the basis of at least the pixel value, the structure of the tissue, the brightness, the contrast, or the like in the actually captured medical image. Therefore, it is easy for the subject to feel the predicted disease state as compared with the case in which the predicted disease image is acquired without being based on the subject's own medical image (for example, a case in which a predicted disease image is generated by normal image rendering software).

Note that the "modification of a medical image with respect to a lesion" in the present disclosure includes at least "addition" of a lesion to a region where no lesion exists, "enlargement" of a lesion, "reduction" of a lesion, "deletion" of a lesion, or the like. That is, the medical image, on which the modification concerning the lesion is to be performed, may be a medical image in which the lesion does not exist or a medical image in which the lesion already exists. In addition, the instruction to designate at least the position or range of the lesion (hereinafter simply referred to as "position/range" in some cases) may be an instruction to designate "addition" of the position/range or an instruction to designate "change" of the position/range.

It is possible to appropriately select a device that executes an image acquisition step, a pre-modification image display step, a lesion reception step, a predicted disease image acquisition step, and a predicted disease image display step. For example, the controller of a personal computer (hereinafter referred to as "PC") may execute all the steps. That is, the controller of the PC may acquire a medical image from the medical image photographing device and execute acquisition and display of a predicted disease image based on the acquired medical image and the like. Furthermore, the controllers of a plurality of devices (for example, at least a medical image photographing device, a PC, a mobile terminal, or a server) may cooperate to execute each step.

In addition, various images can be adopted as pre-modification images. For example, a pre-modification image may be an image indicating the position and range of a lesion on a plain background. Furthermore, a pre-modification image may be an image of a blood vessel of a tissue appearing in a medical image (for example, in a case in which a medical image is a fundus image, an image of a fundus blood vascular is obtained). In this case, an image of the blood vessel may be acquired by extracting the blood vessel from the medical image or may be photographed by an angiography device different from the photographing device that photographs the medical image. In addition, the medical image itself acquired in the image acquisition step may be used as a pre-modification image. Furthermore, in a case in which the medical image is a fundus image, the pre-modification image may be a map image that two-dimensionally shows a distribution (for example, the distribution of the thicknesses of at least one of the layers) related to the structure of the fundus. In this case, the user may designate the position/region of the lesion by designating a region (for example, a region where the thickness of the layer is within a specific range) of a desired structure illustrated in the map image. Furthermore, in a case in which some detection result is acquired by a mathematical model trained by a machine learning algorithm, an attention map may be adopted as a pre-modification image. As will be described in detail later, the attention map indicates the distribution of influence degrees (attention degrees) on the respective positions of influences when a mathematical model obtains detection results in an image region.

In addition, the pre-modification image and the predicted disease image may be the same. That is, by specifying the position and range of a lesion on a medical image or a predicted disease image, the predicted disease image according to specified information may be generated in real time, and the displayed medical image or the predicted disease image may be switched to the newly generated predicted disease image.

The controller may further execute the lesion position acquisition step. In the lesion position acquisition step, when the lesion already exists in the medical image acquired in the image acquisition step, the controller acquires the detection result of the position of the lesion in the medical image. The controller may execute the processing of receiving an instruction in the lesion reception step and the processing of acquiring a predicted disease image in the predicted disease image acquisition step, with the position of the lesion acquired in the lesion position acquisition step as the position of the already existing lesion.

In this case, the user can input various instructions (for example, at least an instruction to enlarge or reduce the range of an already existing lesion, an instruction to change the position of an already existing lesion, an instruction to add a new lesion in addition to an already existing lesion, or the like) according to the position of the already existing lesion. Therefore, an appropriate predicted disease image corresponding to the position of the already existing lesion is acquired.

The controller may further execute the lesion range acquisition step. In the lesion range acquisition step, when the lesion already exists in the medical image acquired in the image acquisition step, the controller acquires the detection result of the range (for example, the shape and size of the lesion without position information) of the lesion in the medical image. The controller may execute the processing of receiving an instruction in the lesion reception step and the processing of acquiring a predicted disease image in the predicted disease image acquisition step, with the range of the lesion acquired in the lesion range acquisition step as the range of the already existing lesion.

In this case, the user can input various instructions (for example, at least an instruction to enlarge or reduce the range of an already existing lesion, an instruction to add a new lesion in addition to an already existing lesion, or the like) according to the range of the already existing lesion. Therefore, an appropriate predicted disease image corresponding to the range of the already existing lesion is acquired.

Note that, when causing the display to display an image prepared for modification in the pre-modification image display step, the controller may display at least the position or range (hereinafter simply referred to as "position/range" in some cases) of the lesion acquired on the basis of the medical image on the pre-modification image as the position/range of the already existing lesion. In this case, the user can input various instructions after appropriately grasping the position/range of the already existing lesion.

A specific method for acquiring the position/range of the already existing lesion in the medical image can be appropriately selected. For example, the controller may acquire the position/range of the lesion output by the mathematical model by inputting the medical image acquired in the image acquisition step to the mathematical model trained by the machine learning algorithm. In this case, the mathematical model may be trained in advance by a training data set in which the data of the medical image is used as the input training data and information indicating the position/range of the lesion included in the input training data is used as the output training data. By using the machine learning algorithm, the position/range of the lesion in the medical image are more appropriately acquired. Furthermore, the controller may acquire the position/range of the lesion in the medical image by executing known image processing on the medical image acquired in the image acquisition step.

However, the technology exemplified in the present disclosure is also useful in a case in which the position/range of the lesion is not detected from a medical image, a case in which the position/range of the lesion cannot be detected from a medical image, and the like. For example, the controller may execute the lesion reception step while the medical image acquired in the image acquisition step is displayed on the display. In this case, even if the position/range of the lesion is not automatically detected, the user can determine or estimate the position/range of the already existing lesion on the basis of the medical image displayed on the display and input various instructions on the basis of the determination or estimation result. In addition, in a case in which there is no lesion in the acquired medical image, a predicted disease image to which a lesion has been added according to the specified information may be acquired on the basis of the medical image.

In the lesion reception step, the controller may receive an instruction to designate the type (that is, the type of disease) of a lesion to be modified. In a case in which the type of lesion is designated, the controller may acquire a predicted disease image with the lesion of the designated type being modified on the basis of the medical image. In this case, for example, in a case in which a lesion is newly added to the medical image, the user can appropriately select the type of lesion to be added. Furthermore, the user can change the type of lesion in the medical image. Therefore, the predicted disease image is more appropriately acquired.

Furthermore, in the lesion reception step, the controller may receive an instruction to designate the degree of disease (progress status) of the lesion to be modified. When the degree of disease is designated, the controller may acquire the predicted disease image obtained by modifying the color of the lesion to a color (including color density, color distribution roughness, and the like) corresponding to the designated degree of disease on the basis of the medical image. In this case, the lesion whose color is changed according to the degree of disease is also appropriately displayed on the predicted disease image.

The controller may further execute the lesion type acquisition step. In the lesion type acquisition step, when the lesion already exists in the medical image acquired in the image acquisition step, the controller acquires the detection result of the type of already existing lesion. The controller may execute the processing of receiving an instruction in the lesion reception step and the processing of acquiring a predicted disease image in the predicted disease image acquisition step with the type of lesion acquired as the type of already existing lesion when the type of lesion is acquired in the lesion type acquisition step.

In this case, the user can input various instructions (for example, at least an instruction to enlarge or reduce the range of the already existing lesion, an instruction to add the same type of lesion as the already existing lesion to another position, or the like) according to the type of already existing lesion. Therefore, an appropriate predicted disease image corresponding to the type of the already existing lesion is acquired.

Note that the controller may cause the display to display the type of lesion acquired in the lesion type acquisition step. In this case, the user can input various instructions after appropriately grasping the type of already existing lesion.

A specific method for acquiring the type of already existing lesion in the medical image can be appropriately selected. For example, the controller may acquire the type of lesion output by the mathematical model by inputting the medical image acquired in the image acquisition step to the mathematical model trained by the machine learning algorithm. In this case, the mathematical model may be trained in advance by a training data set in which the data of the medical image is used as the input training data and information indicating the type of lesion included in the input training data is used as the output training data. By using the machine learning algorithm, the type of lesion in the medical image are more appropriately acquired.

In a case in which the range of the lesion is designated, the controller may acquire a predicted disease image in which the range of the lesion is between the designated range and the range of the lesion in the medical image acquired in the image acquisition step together with the predicted disease image in which the lesion in the designated range is modified. In this case, a transition in which the range of the lesion is enlarged or reduced is more appropriately grasped from a plurality of predicted disease images acquired based on the medical image of the subject himself/herself.

It is possible to appropriately select a method of displaying a plurality of predicted disease images having different lesion ranges on the display. For example, the controller may sequentially switch (for example, in a moving image) and display each of the plurality of predicted disease images in chronological order. In this case, the medical image (that is, a raw image in which a lesion is not modified) acquired in the image acquisition step may be displayed before the plurality of predicted disease images. In addition, the controller may display a plurality of predicted disease images side by side at the same time. In this case, a raw image may also be displayed in addition to the plurality of predicted disease images.

In the predicted disease image acquisition step, the controller may acquire a predicted disease image including an image of a lesion predicted from information of the lesion on the basis of information of the lesion including at least the position or range and an image of a tissue of a subject. The information of the lesion is set according to the instruction received in the lesion reception step. In this case, the image of the lesion predicted from the information designated by the user is appropriately acquired on the basis of the image of the tissue of the subject. Therefore, it is easy for the subject to realize the predicted disease state.

In the predicted disease image acquisition step, the controller may acquire a predicted disease image by inputting an image of the tissue of the subject and the information of the lesion to the mathematical model trained by the machine learning algorithm. In this case, using a mathematical model trained by a plurality of training data including an actual medical image makes it easy to acquire a predicted disease image approximate to the actual medical image as compared with a case of using a function or the like that does not use a machine learning algorithm.

When a machine learning algorithm is utilized, the mathematical model may have been trained by a plurality of training data sets. The training data set may include training data for input and training data for output (e.g., correct data). The training data for output may be a medical image of a tissue including a lesion photographed by the medical image photographing device. The training data for input may include a lesion removed image obtained by removing information of a lesion from the training data for output and information of a lesion in the training data for output (for example, information indicating at least a position, a range, or a type of lesion). In this case, the mathematical model for outputting a predicted disease image is appropriately trained based on the actually photographed medical image.

A medical image may be a fundus image (for example, a fundus front image obtained by photographing the fundus from the line-of-sight direction, a fundus tomographic image including information in the depth direction of the fundus, or the like) obtained by photographing the fundus of the eye to be examined. For example, in a case in which a medical image is a fundus front image, training data for output may be an image including a lesion photographed by a fundus photographing device (for example, a fundus camera, a scanning laser ophthalmoscope (SLO), or an OCT device) that photographs a fundus front image. In addition, a lesion removed image used as training data for input may be an image of a fundus vascular image. An image of the fundus blood vessel may be acquired by extracting the fundus blood vessel from a fundus front image or may be photographed by a device different from a fundus photographing device that photographs a fundus front image. The information of a lesion used as training data for input may be generated, for example, by specifying the position and range of the lesion in an image by the operator who looks at training data for output (fundus front image). In addition, the information of a lesion may be acquired by inputting training data for output to a mathematical model trained in advance to input a fundus front image and output the information of the lesion. In addition, information such as the position and range of a lesion may be acquired by performing known image processing on the fundus front image.

However, the controller can also acquire a predicted disease image without using any machine learning algorithm. For example, the controller may generate a predicted disease image from a medical image by converting at least part of the medical image according to designated information (information of the designated lesion).

Furthermore, the controller of the medical image processing device may output a medical image and designated information to another device (for example, a server) storing a program for implementing a mathematical model. A device at the output destination of a medical image may acquire a predicted disease image by inputting an input medical image and specified information to a mathematical model and output the acquired predicted disease image to the medical image processing device.

DESCRIPTION OF EMBODIMENTS (Device Configuration)

Figure 1:
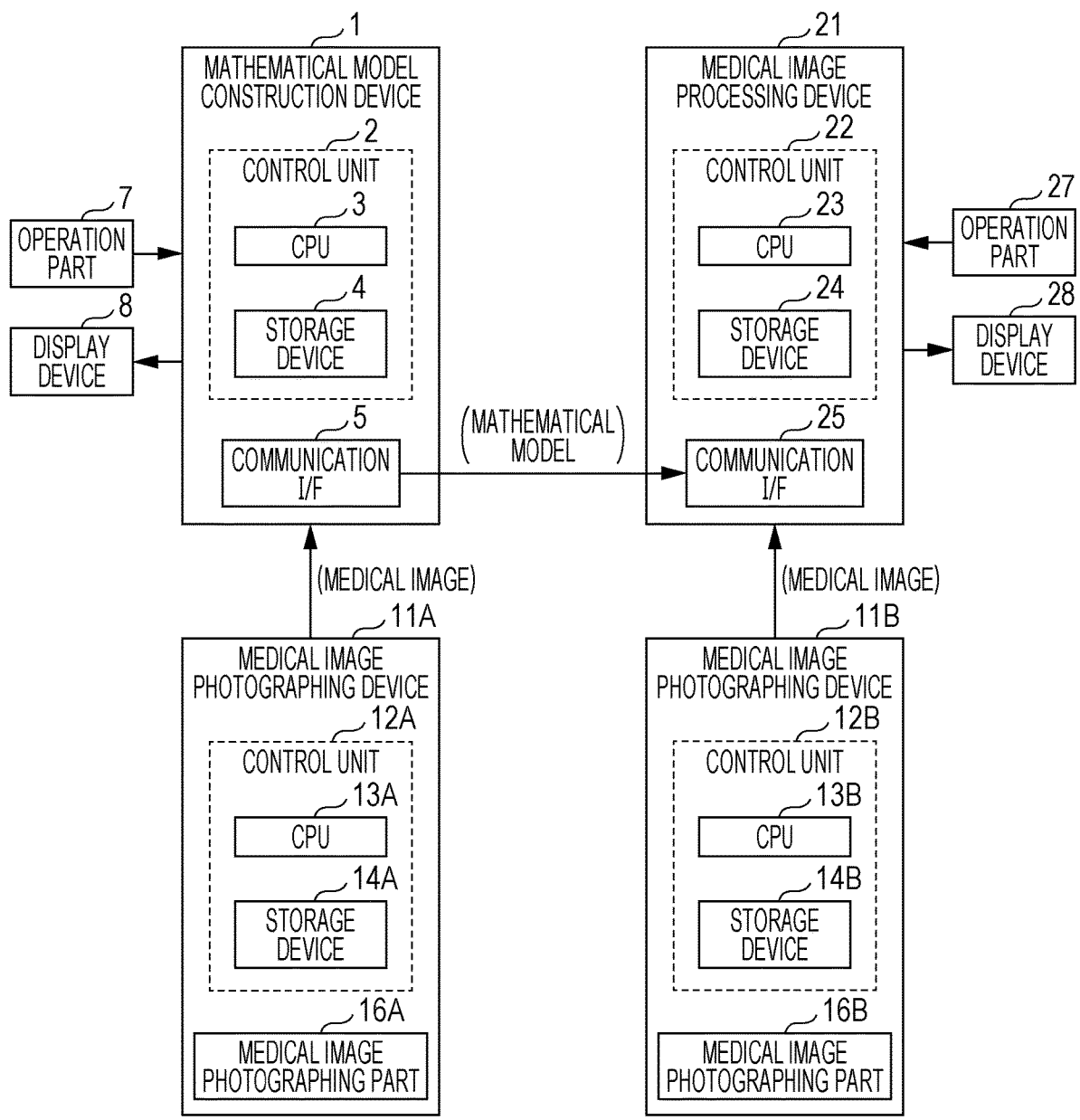
FIG. 1 is a block diagram illustrating the schematic configurations of a mathematical model construction device 1, a medical image processing device 21, and medical image photographing devices 11A and 11B.

One embodiment of the present disclosure will be described below with reference to the accompanying drawings. As illustrated in FIG. 1, the present embodiment uses a mathematical model construction device 1, a medical image processing device 21, and medical image photographing devices 11A and 11B. The mathematical model construction device 1 constructs a mathematical model by training the mathematical model by a machine learning algorithm. The constructed mathematical model outputs information according to the training contents based on the input information (details of the mathematical model will be described later with reference to FIG. 2). The medical image processing device 21 executes various types of processing for acquiring a predicted disease image 60 (see FIGS. 2 and 3) using the mathematical model. The predicted disease image 60 is an image indicating a tissue state in a case in which the disease is predicted to occur, a tissue state in a case in which the disease is predicted to progress, a tissue state in a case in which the disease is predicted to cure, or the like. The predicted disease image 60 is acquired based on the actually photographed image of the tissue of the subject. The medical image photographing devices 11A and 11B photographs a medical image 30 (see FIGS. 2 and 3) which is an image of a tissue of a subject.

Note that the present embodiment will exemplify a case in which two-dimensional fundus front images obtained by photographing the fundus tissue of the eye to be examined from the line-of-sight direction of the eye to be examined are used as the medical image 30 and the predicted disease image 60. However, at least part of the technology exemplified by the present disclosure can be applied to even a case in which the medical image 30 and the predicted disease image 60 are images other than fundus front images. For example, the medical image 30 and the predicted disease image 60 may be two-dimensional tomographic images or three-dimensional tomographic images including information in the depth direction of the fundus of the subject eye. The medical image 30 and the predicted disease image 60 may be ophthalmic images of tissues other than the fundus of the eye to be examined (anterior segment images). Furthermore, the medical image 30 and the predicted disease image 60 may be medical images of a living tissue other than the eye to be examined (for example, images of internal organs).

For example, a personal computer (hereinafter referred to as a "PC") is used as the mathematical model construction device 1 according to the present embodiment. Although details will be described later, the mathematical model construction device 1 constructs a mathematical model by training the mathematical model using the medical image acquired from the medical image photographing device 11A. However, the device that can function as the mathematical model construction device 1 is not limited to the PC. For example, the medical image photographing device 11A may function as the mathematical model construction device 1. In addition, controllers (for example, the CPU of the PC and the CPU 13A of the medical image photographing device 11A) of a plurality of devices may cooperate to construct a mathematical model.

In addition, a PC is used as the medical image processing device 21 according to the present embodiment. However, the device that can function as the medical image processing device 21 is not limited to the PC. For example, the medical image photographing device 11B, a server, or the like may function as the medical image processing device 21. In addition, a portable terminal such as a tablet terminal or a smartphone may function as the medical image processing device 21. The controllers (for example, the CPU of the PC and the CPU 13B of the medical image photographing device 11B) of the plurality of devices may perform various types of processing in cooperation.

In addition, the present embodiment will exemplify a case in which a CPU is used as an example of a controller that performs various processes. Obviously, however, a controller other than the CPU may be used for at least some of the various devices. For example, by adopting a GPU as the controller, the processing speed may be increased.

The mathematical model construction device 1 will be described. The mathematical model construction device 1 is provided for, for example, a manufacturer that provides the medical image processing device 21 and a medical image processing program to a user. The mathematical model construction device 1 includes a control unit 2 that performs various control processes and a communication I/F 5. The control unit 2 includes a CPU 3 that is a controller configured to perform control and a storage device 4 that can store programs, data, and the like. The storage device 4 stores a mathematical model construction program for constructing a mathematical model. In addition, the communication I/F 5 connects the mathematical model construction device 1 to another device (for example, the medical image photographing device 11A, the medical image processing device 21, or the like).

The mathematical model construction device 1 is connected to an operation part 7 and a display device 8. The operation part 7 is operated by the user in order for the user to input various instructions to the mathematical model construction device 1. As the operation part 7, for example, at least one of a keyboard, a mouse, and a touch panel can be used. Note that a microphone or the like for inputting various instructions may be used together with the operation part 7 or instead of the operation part 7. The display device 8 displays various images. Various devices (for example, at least one of a monitor, a display, and a projector) that can display an image can be used as the display device 8. Note that the "image" in the present disclosure includes both a still image and a moving image.

The mathematical model construction device 1 can acquire information (to be sometimes simply referred to as a "medical image") of the medical image 30 from the medical image photographing device 11A. The mathematical model construction device 1 may acquire the information of the medical image 30 from the medical image photographing device 11A via, for example, at least one of wired communication, wireless communication, and a removable storage medium (for example, a USB memory).

The medical image processing device 21 will be described. The medical image processing device 21 is installed, for example, in a facility (for example, a hospital or a health examination facility) that performs diagnosis, examination, or the like of a subject. The medical image processing device 21 includes a control unit 22 that performs various control processes and a communication I/F 25. The control unit 22 includes a CPU 23 that is a controller configured to perform control and a storage device 24 that can store programs, data, and the like. The storage device 24 stores a medical image processing program for executing medical image processing (see FIG. 4) to be described later. The medical image processing program includes a program for implementing the mathematical model constructed by the mathematical model construction device 1. The communication I/F 25 connects the medical image processing device 21 to another device (for example, the medical image photographing device 11B or the mathematical model construction device 1).

The medical image processing device 21 is connected to an operation part 27 and a display device 28. Various devices can be used as the operation part 27 and the display device 28 similarly to the operation part 7 and the display device 8 described above.

The medical image processing device 21 can acquire the medical image 30 from the medical image photographing device 11B. The medical image processing device 21 may acquire the medical image 30 from the medical image photographing device 11B via, for example, at least one of wired communication, wireless communication, and a removable storage medium (for example, a USB memory). Furthermore, the medical image processing device 21 may acquire a program or the like for implementing the mathematical model constructed by the mathematical model construction device 1 via communication or the like.

The medical image photographing devices 11A and 11B will be described. The following is an example in which the present embodiment uses the medical image photographing device 11A that provides the medical image 30 to the mathematical model construction device 1 and the medical image photographing device 11B that provides the medical image 30 to the medical image processing device 21. However, the number of medical image photographing devices used is not limited to two. For example, the mathematical model construction device 1 and the medical image processing device 21 may acquire the medical images 30 from a plurality of medical image photographing devices. In addition, the mathematical model construction device 1 and the medical image processing device 21 may acquire the medical image 30 from one common medical image photographing device. Note that the two medical image photographing devices 11A and 11B exemplified in the present embodiment have the same configuration. Accordingly, the two medical image photographing devices 11A and 11B will be collectively described below.

A medical image photographing device 11 (11A, 11B) includes a control unit 12 (12A, 12B) that performs various control processes and a medical image photographing part 16 (16A, 16B). The control unit 12 includes a CPU 13 (13A, 13B), which is a controller that performs control, and a storage device 14 (14A, 14B) that can store programs, data, and the like.

The medical image photographing part 16 has various configurations necessary for photographing the medical image (fundus front image in the present embodiment) 30 of the tissue of the subject. For example, in a case in which the medical image photographing device 11 is a fundus camera, the medical image photographing part 16 includes an illumination optical system, a light receiving optical system, a photographing element, and the like for photographing a front image of the fundus of the subject. Note that the device that can be used as the medical image photographing device 11 is not limited to the fundus camera. For example, a scanning laser ophthalmoscope (SLO), an OCT device, a corneal endothelial cell photographing device (CEM), a computed tomography (CT) device, or the like may be used as the medical image photographing device 11.

(Model Structure of Mathematical Model)

Figure 2:
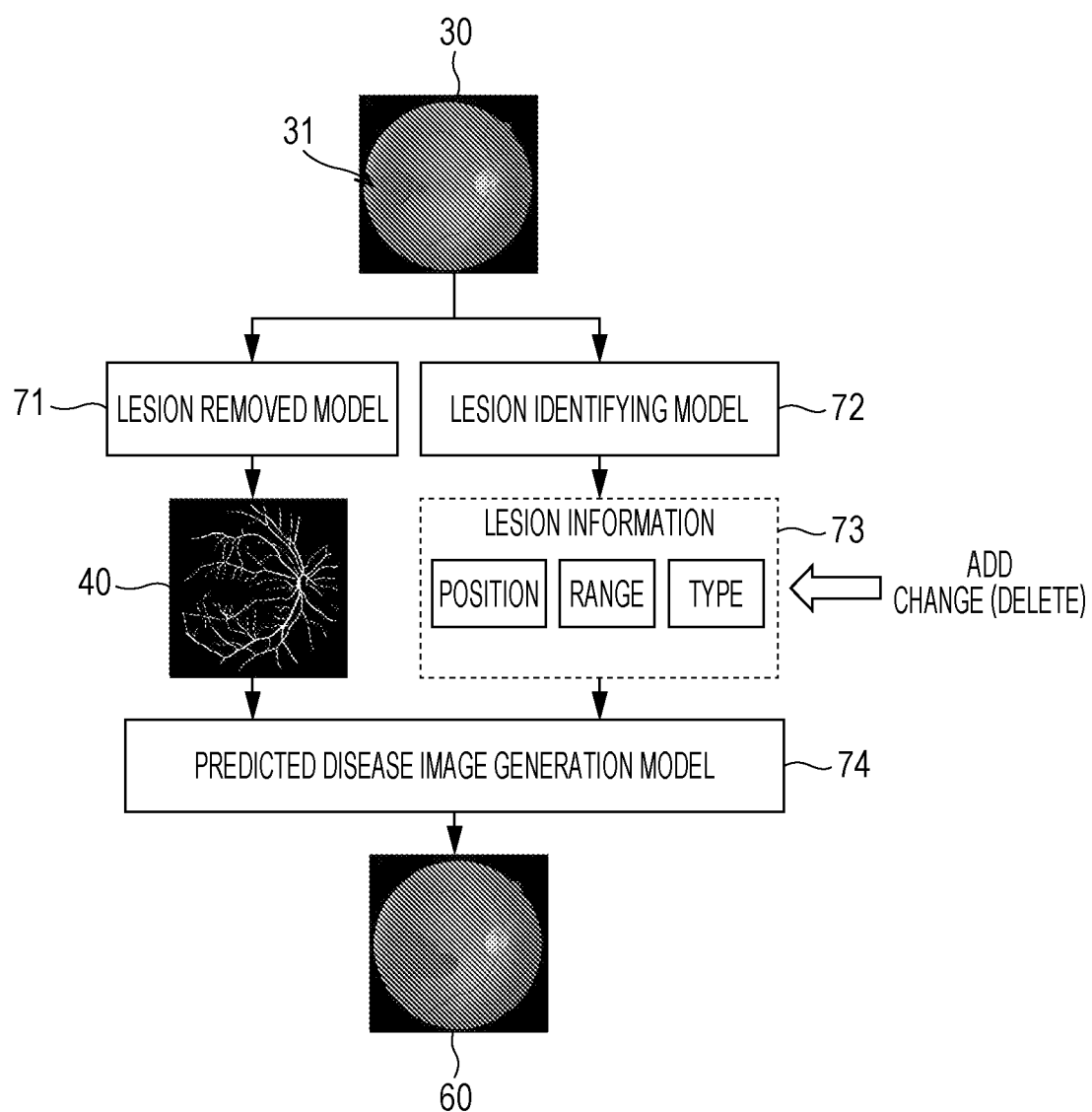
FIG. 2 is an explanatory diagram for explaining a model structure according to the present embodiment for acquiring a predicted disease image 60.

A model structure of a mathematical model according to the present embodiment for the medical image processing device 21 to acquire the predicted disease image 60 will be described with reference to FIG. 2. In the present embodiment, a lesion removal model 71, a lesion identifying model 72, and a predicted disease image generation model 74 are used as mathematical models for acquiring the predicted disease image 60.

By inputting the medical image 30, the lesion removal model 71 outputs a lesion removed image 40 obtained by removing the information of a lesion 31 from the medical image 30. As the lesion removed image 40, various images that do not include the information of the lesion 31 and include the information of the structure of the tissue can be adopted. In the present embodiment, an image of a blood vessel (fundus vascular image) which is one of the structures of the tissue is used as the lesion removed image 40.

Upon receiving the medical image 30, the lesion identifying model 72 outputs a detection result (lesion information 73) of the lesion 31 if the lesion 31 exists in the medical image 30. In the present embodiment, the lesion information 73 output by the lesion identifying model 72 includes information of the position of the lesion 31, information of the range of the lesion 31, and information of the type (that is, the type of disease) of the lesion 31. Although details will be described later, when the predicted disease image 60 is acquired, at least addition or change (including deletion) of the lesion information 73 is executed according to an instruction input from the user.

As an example, the lesion identifying model 72 according to the present embodiment outputs an attention map 80 (see FIG. 3) when obtaining a detection result of the type of the lesion 31 included in the medical image 30. Information of the position and range of the lesion 31 is obtained from the attention map 80. The attention map 80 indicates the distribution of influence degrees (attention degrees) at the respective positions of influences imposed when the lesion identifying model 72 obtains the detection result of the type of the lesion 31 in the image region. A region having a high influence degree strongly affects the detection result of the type of the lesion 31 as compared with a region having a low influence degree. An example of the attention map 80 is described in, for example, the following paper or the like. "Ramprasaath R. Selvaraju, et al. "Grad-CAM: Visual Explanations from Deep Networks via Gradient-based Localization" Proceedings of the IEEE International Conference on Computer Vision, 2017-October, pp. 618-626"

However, it is also possible to change the method of acquiring information of the position and range of the lesion 31. For example, information of the position and range of the lesion 31 may be acquired by executing known image processing on the medical image 30 and segmenting the region of the lesion 31.

The predicted disease image generation model 74 outputs the predicted disease image 60 by inputting the lesion removed image 40 and the lesion information 73 for which at least addition, change, or deletion has been executed. As described above, the lesion removed image 40 does not include information of the lesion 31. Accordingly, using the lesion removed image 40 and the lesion information 73 according to the instruction input from the user makes the predicted disease image generation model 74 properly output the predicted disease image 60 desired by the user.

In the present embodiment, the predicted disease image 60 is acquired on the basis of at least one (in the present embodiment, the structure of the tissue indicated by the lesion removed image 40 acquired from the medical image 30) of the pixel value, the structure of the tissue, the brightness, the contrast, and the like of the actually photographed medical image 30. Accordingly, it is easy for the subject to feel the predicted disease state as compared with the case in which the predicted disease image is acquired without being based on the medical image 30 of the subject himself/herself.

Furthermore, in the present embodiment, the predicted disease image 60 including the image of the lesion 31 predicted from the lesion information 73 is acquired on the basis of the actually photographed medical image 30 and the lesion information 73 including the information of the position and the range. Therefore, the image of the lesion 31 predicted from the information designated by the user is appropriately acquired on the basis of the image of the tissue of the subject.

An example of the mathematical model construction processing executed by the mathematical model construction device 1 will be described. The CPU 3 of the mathematical model construction device 1 constructs a mathematical model by executing training of a mathematical model using a training data set by a machine learning algorithm. A program for implementing the constructed mathematical model is stored in the storage device 24 of the medical image processing device 21. As the machine learning algorithm, for example, a neural network, a random forest, boosting, a support vector machine (SVM), and the like are generally known.

A neural network is a technique that mimics the behavior of a biological neuronal network. Neural networks include, for example, a feedforward (forward propagation type) neural network, a RBF network (radiation basis function), a spiking neural network, a convolutional neural network, a recursive neural network (recurrent neural net, feedback neural net, or the like), and a probabilistic neural network (Boltzmann machine, Bayesian network, or the like).

Random forest is a method of performing learning based on randomly sampled training data to generate a large number of decision trees. In the case of using random forest, branches of a plurality of decision trees learned in advance as identifiers are followed, and an average (or majority decision) of results obtained from the respective decision trees is taken.

Boosting is a method of generating a strong identifier by combining a plurality of weak identifiers. A strong identifier is constructed by sequentially learning a simple weak identifier.

The SVM is a method of configuring a two-class pattern identifier using a linear input element. The SVM learns the parameters of the linear input element based on, for example, a criterion (hyperplane separation theorem) of obtaining a margin maximizing hyperplane having the maximum distance from the training data to each data point.

In the present embodiment, each mathematical model is constructed by a generative adversarial network (GAN) that uses two competing neural networks, a convolutional neural network (CNN) that is a type of multilayer neural network, and the like.

A mathematical model refers, for example, to a data structure for predicting a relationship between input data and output data. The mathematical model is constructed by being trained using a plurality of training data sets. The training data set is a set of training data for input and training data for output. The mathematical model is trained such that when certain training data for input is input, corresponding training data for output is output. For example, training updates the correlation data (for example, a weight) between each input and each output.

An example of a method of constructing the lesion removal model 71 will be described. In the present embodiment, when constructing the lesion removal model 71, the CPU 3 of the mathematical model construction device 1 trains the mathematical model using the medical image 30 of the subject photographed by the medical image photographing device 11A as training data for input and using the lesion removed image (fundus vascular image in the present embodiment) 40 of the same subject as training data for output. For example, the lesion removed image 40 may be photographed by the medical image photographing device 11A by a method different from the method of photographing the medical image 30, or may be photographed by a device different from the medical image photographing device 11A. In addition, the lesion removed image 40 may be extracted from the medical image 30 by known image processing. Furthermore, the lesion removed image 40 may be extracted from the medical image 30 according to an instruction input from the user.

An example of a method of constructing the lesion identifying model 72 will be described. In the present embodiment, when constructing the lesion identifying model 72, the CPU 3 trains the mathematical model using the medical image 30 of the subject photographed by the medical image photographing device 11A as training data for input and using information (in the present embodiment, information of the position of the lesion 31, information of the range of the lesion 31, and information of the type of the lesion 31) of the lesion 31 in the training data for input (medical image 30) as training data for output. For example, the information of the lesion 31 may be generated according to an instruction input from the user who has confirmed the training data for input (medical image 30). Furthermore, at least part of the information of the lesion 31 (for example, position and range information) may be generated by executing known image processing on the training data for input.

An example of a method of constructing the predicted disease image generation model 74 will be described. In the present embodiment, when constructing the predicted disease image generation model 74, the CPU 3 uses the medical image 30 of the subject photographed by the medical image photographing device 11A as training data for output. In addition, the CPU 3 uses, as training data for input, the lesion removed image 40 obtained by removing the information of the lesion 31 from the training data for output (the medical image 30) and the information of the lesion 31 related to the training data for output (in the present embodiment, information of the position of the lesion 31, information of the range of the lesion 31, and information of the type of the lesion 31). As a method by which the CPU 3 acquires the lesion removed image 40 and the information of the lesion 31, a method similar to the above-described method can be adopted.

(Predicted Disease Image Acquisition Screen)

An example of a predicted disease image acquisition screen 9 displayed on the display device 28 will be described with reference to FIG. 3. The predicted disease image acquisition screen 9 is displayed on the display device 28 when the user causes the medical image processing device 21 to generate the predicted disease image 60 of the subject.

On the predicted disease image acquisition screen 9 according to the present embodiment, the medical image 30, the lesion removed image 40, the attention map 80, a pre-modification image 50, the predicted disease image 60, an addition/deletion selector 91, and a lesion type display 92 are displayed.

The medical image 30 is an image of the tissue of the subject actually photographed by the medical image photographing device 11B (see FIG. 1). Including the medical image 30 in the predicted disease image acquisition screen 9 allows the user to easily grasp the state of the tissue appearing in the actually photographed medical image 30 and the state of the tissue appearing in the predicted disease image 60.

As described above, the lesion removed image 40 is an image (fundus vascular image in the present embodiment) obtained by removing the information of the lesion 31 from the medical image 30. Including the lesion removed image 40 in the predicted disease image acquisition screen 9 allows the user to grasp the structure of the tissue of the subject and then input an appropriate instruction to generate the predicted disease image 60 to the medical image processing device 21.

As described above, the attention map 80 indicates the distribution of influence degrees (attention degrees) at the respective positions of influences imposed when the lesion identifying model 72 obtains the detection result of the type of the lesion 31. Therefore, the attention map 80 shows the position and range of the lesion 31 appearing in the medical image 30. Accordingly, including the attention map 80 in the predicted disease image acquisition screen 9 allows the user to input an appropriate instruction to the medical image processing device 21 after grasping the position and range of the lesion 31 actually existing in the tissue of the subject.

At least the position or range of the lesion 31 (see FIG. 2) to be modified on the medical image 30 is displayed on the pre-modification image 50. The pre-modification image 50 according to the present embodiment is an image illustrating at least the position or range (in the present embodiment, both the position and range) of the lesion 31 on a plain background. Note that, in a state before an instruction to add or change (including deletion) the position or range of the lesion 31 is input, the position and range of the lesion 31 appearing in the attention map 80 are indicated in the pre-modification image 50. When an instruction to add or change the position or range is input, the position/range of the lesion 31 in the pre-modification image 50 is changed according to the input instruction. The pre-modification image 50 exemplified in FIG. 3 is an image after an instruction to change the position/range of the lesion 31 is input.

The predicted disease image 60 is an image indicating a predicted tissue state. When an instruction to designate the lesion 31 is input by the user, the predicted disease image 60 generated according to the designated information is displayed on the display device 28 in real time.

The addition/deletion selector 91 is displayed to make the user input an instruction to switch between a case of newly adding the lesion 31 and a case of deleting the lesion 31. In the present embodiment, when the user inputs an instruction to select "Insert", the lesion 31 can be newly added. When the user inputs an instruction to select "Delete", the lesion 31 can be deleted.

The lesion type display 92 displays the type of the lesion 31 already existing in the photographed medical image 30. Furthermore, switching the type of the lesion 31 displayed on the lesion type display 92 allows the user to input, to the medical image processing device 21, an instruction to designate the type of the lesion 31 to be newly added and an instruction to change the type of the lesion 31 set at that time.

Figure 3:
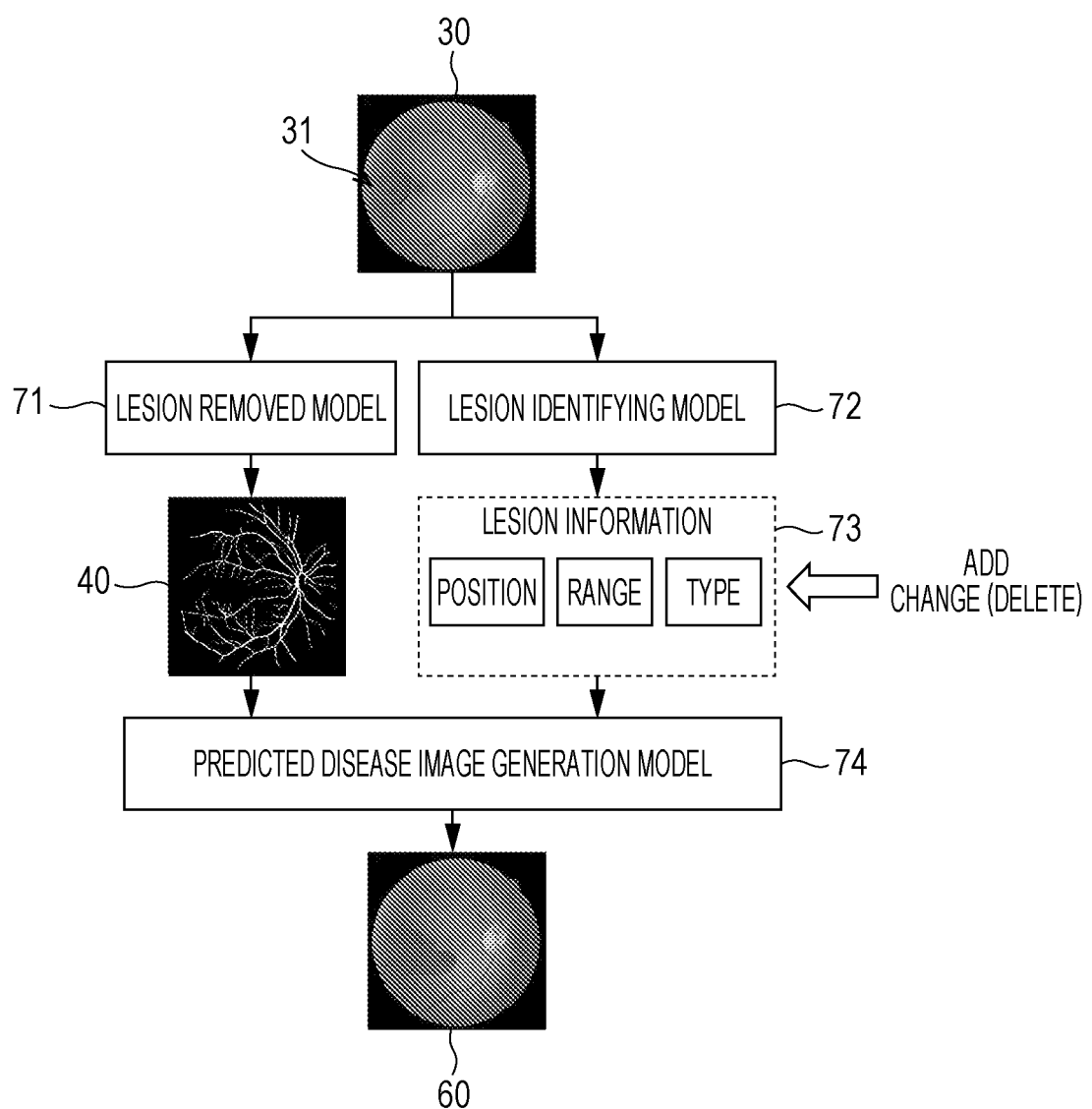
FIG. 3 is a diagram illustrating an example of a predicted disease image acquisition screen 9 displayed on a display device 28.

Note that the predicted disease image acquisition screen 9 illustrated in FIG. 3 is merely an example. That is, the configuration of the predicted disease image acquisition screen 9 can be appropriately changed. First of all, the configuration of the pre-modification image 50 can be changed. In a pre-modification image, only the position of the lesion 31 (for example, the position of the center of the lesion 31) may be displayed. In this case, the range of the lesion 31 may be displayed with a parameter (for example, a numerical value indicating the breadth of the range) other than the image. In addition, the position and range of the lesion 31 may be displayed in different pre-modification images. When, for example, the position of the lesion 31 is determined in advance, only the range (shape and size) of the lesion 31 may be displayed in the pre-modification image.

In addition, various images can be used as pre-modification images. For example, the lesion removed image 40 may be used as a pre-modification image, or the medical image 30 actually photographed by the medical image photographing device 11B (see FIG. 1) may be used as a pre-modification image. In addition, an image photographed by a device different from the medical image photographing device 11B that has photographed the medical image 30 may be used as a pre-modification image. In addition, the pre-modification image and the predicted disease image 60 may be the same. That is, by specifying the position and range of the lesion 31 on the medical image 30 or the predicted disease image 60, the predicted disease image 60 according to the specified information may be generated in real time, and the displayed medical image 30 or the predicted disease image 60 may be switched to the newly generated predicted disease image 60. In addition, the pre-modification image and the predicted disease image 60 may be switched and displayed. The lesion removed image 40 may not be displayed on the display device 28 during the execution of medical image processing (see FIG. 4).

In the present embodiment, the pre-modification image 50 and the predicted disease image 60 are displayed on the same display device 28. However, the pre-modification image 50 and the predicted disease image 60 may be displayed on different display devices simultaneously or in a switched manner. For example, the pre-modification image 50 may be displayed on a display device visually recognized by a doctor or the like, and the predicted disease image 60 may be displayed on a display device visually recognized by a subject or the like.

(Medical Image Processing)

Medical image processing executed by the medical image processing device 21 according to the present embodiment will be described with reference to FIGS. 3 and 4. The medical image processing is executed by the CPU 23 according to the medical image processing program stored in the storage device 24. When the user inputs an instruction to start generation and display of the predicted disease image 60, the CPU 23 starts the medical image processing illustrated in FIG. 4.

Figure 4:
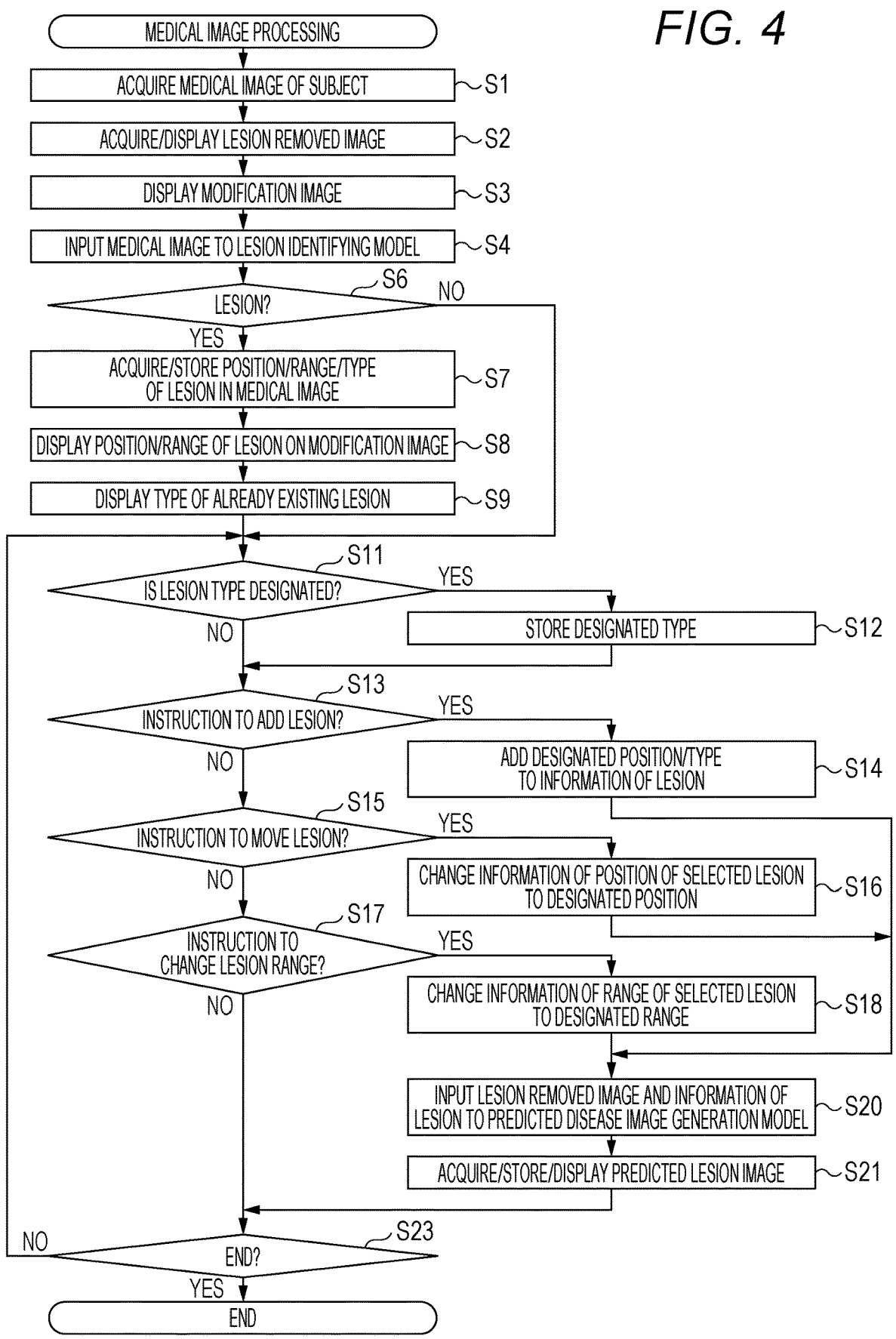
FIG. 4 is a flowchart of medical image processing executed by the medical image processing device 21.

As illustrated in FIG. 4, upon starting the medical image processing, the CPU 23 acquires the medical image 30 (see FIG. 2) of the subject (S1). As described above, the medical image 30 according to the present embodiment is an image of the tissue of the subject actually photographed by the medical image photographing device 11B. The CPU 23 causes the display device 28 to display the medical image 30 acquired in S1 (more specifically, in the predicted disease image acquisition screen 9 in the present embodiment)

The CPU 23 acquires the lesion removed image 40 of the same tissue as the photographing target of the medical image 30 and causes the display device 28 to display the image (S2). As described above, the CPU 23 according to the present embodiment acquires the lesion removed image 40 by inputting the medical image 30 acquired in S1 to the lesion removal model 71 (see FIG. 2). Therefore, the lesion removed image 40 is more appropriately acquired as compared with a case of using a method not using a machine learning algorithm (for example, known image processing). However, it is also possible to change the method of acquiring the lesion removed image 40. For example, the lesion removed image 40 may be photographed by the medical image photographing device 11A by a method different from the method of photographing the medical image 30, or may be photographed by a device different from the medical image photographing device 11A. In addition, the lesion removed image 40 may be extracted from the medical image 30 by known image processing. Furthermore, the lesion removed image 40 may be extracted from the medical image 30 according to an instruction input from the user.

The CPU 23 then displays the pre-modification image 50 (see FIG. 3) on the display device 28 (S3). As described above, the pre-modification image 50 may be the lesion removed image 40, the medical image 30, or the like The CPU 23 then inputs the medical image 30 acquired in S1 to the lesion identifying model 72 (S4). When the lesion 31 already exists in the input medical image 30, the lesion identifying model 72 according to the present embodiment outputs the lesion information 73 (detection result of at least the range or type of the lesion 31). On the other hand, when the lesion 30 does not exist in the medical image 30, the lesion information 73 is not output. If the lesion 31 does not exist in the medical image 30 acquired in S1 (S6: NO), the process directly proceeds to S11.

When the lesion 31 is present in the medical image 30 acquired in S1 (S6: YES), the CPU 23 acquires the lesion information 73 output by the lesion identifying model 72 and stores the same in the storage device 24 (S7). As a result, the processing in S11 to S21 described later is executed with the position, range, and type of the lesion 31 acquired in S7 as the position, range, and type of the already existing lesion 31. Therefore, the user can appropriately input various instructions to the medical image processing device in accordance with the position, range, and type of the already existing lesion 31. In addition, the CPU 23 displays the position and range of the already existing lesion 31 in the medical image 30 on the pre-modification image 50 based on the lesion information 73 acquired in S7 (S8). Furthermore, in the present embodiment, the CPU 23 causes the display device 28 to display the attention map 80 (see FIG. 3) obtained by the lesion identifying model 72. The CPU 23 causes the lesion type display 92 (see FIG. 3) to display the type of the lesion 31 already existing in the medical image 30 on the basis of the lesion information 73 acquired in S7 (S9). Therefore, the user can appropriately grasp the position, range, and type of the already existing lesion 31 and then input various instructions to the medical image processing device 21.

The CPU 23 then determines whether or not an instruction to designate the type (for example, the type of the lesion 31 to be newly added to the predicted disease image 60) of the lesion 31 to be modified has been input (S11). Upon receiving the instruction to designate the type of the lesion 31

(S11: YES), the CPU 23 stores the designated type of the lesion 31 in the storage device 23 (S12). The process proceeds to S13.

The CPU 23 then determines whether an instruction to newly add the lesion 31 to the predicted disease image 60 has been input (S13). For example, in the present embodiment, in a state in which the type of the lesion 31 is designated, the user can input an instruction to add the lesion 31 to a desired position by moving the cursor to the desired position on the pre-modification image 50 and operating the operation part 27. Upon receiving an instruction to add the lesion 31 (S13: YES), the CPU 23 adds information of the position and type of the designated lesion 31 to the lesion information 73 (see FIG. 2) (S14). In addition, the CPU 23 displays the position of the lesion 31 added in S14 on the pre-modification image 50 (see FIG. 3). Thereafter, the process proceeds to S20 (described later).

If an instruction to add the lesion 31 is not input (S13: NO), the CPU 23 determines whether an instruction to move the position of the lesion 31 is input (S15). For example, in the present embodiment, the user can input an instruction to designate the movement position of the lesion 31 by dragging the position of the lesion 31 on the pre-modification image 50 to a desired position. Upon receiving the movement instruction (S15: YES), the CPU 23 changes the information of the position of the selected lesion 31 in the lesion information 73 (see FIG. 2) to the position designated in S15 (S16). In addition, the CPU 23 moves the position of the lesion 31 displayed on the pre-modification image 50 (see FIG. 3) on the basis of the information of the position of the lesion 31 changed in S16. Thereafter, the process proceeds to S20 (described later).

When an instruction to move the lesion 31 has not been input (S15: NO), the CPU 23 determines whether an instruction to change (enlarge, reduce, or delete) the range of the lesion 31 has been input (S17). For example, in the present embodiment, the user can input an instruction to designate enlargement or reduction of the range of the lesion 31 by dragging the frame portion of the lesion 31 on the pre-modification image 50 in a desired direction. In addition, the user can input an instruction to designate deletion of the selected lesion 31 by operating the deletion button in a state in which the lesion 31 on the pre-modification image 50 is selected. If an instruction to change the range of the lesion 31 is input (S17: YES), the CPU 23 changes (enlarge, reduce, or delete) the information of the range of the selected lesion 31 in the lesion information 73 (see FIG. 2) to the range designated in S17 (S18). In addition, the CPU 23 changes the range of the lesion 31 displayed on the pre-modification image 50 (see FIG. 3) on the basis of the information of the range of the lesion 31 changed in S18. Thereafter, the process proceeds to S20.

When the instruction to designate the lesion 31 is received in S13, S15, or S17 or the lesion information 73 is added or changed in S14, S16, or S18, the CPU 23 acquires the predicted disease image 60 in which the lesion 31 is modified according to the designated information based on the medical image 30 acquired in S1 (S20, S21). More specifically, in S20 in the present embodiment, the CPU 23 inputs the lesion removed image 40 acquired in S2 on the basis of the medical image 30 and the added or changed lesion information 73 to the predicted disease image generation model 74 (see FIG. 2). In S21, the CPU 23 acquires the predicted disease image 60 output by the predicted disease image generation model 74, stores the predicted disease image in the storage device 24, and displays the predicted disease image on the display device 28 (the predicted disease image acquisition screen 9 according to the present embodiment). That is, the CPU 23 causes the display device 28 to display the newly acquired predicted disease image 60 in real time while causing the display device 28 to display the pre-modification image 50.

Note that, in S20 and S21 in the present embodiment, the CPU 23 can acquire the predicted disease image 60 in which the lesion 31 at the designated position/range is modified and the predicted disease image 60 in the middle of transition of the state of the lesion 31 (hereinafter referred to as an "image during transition"). The image during transition is an image in which the position/range of the lesion 31 is between the position/range designated in S13, S15, or S17 and the position/range of the lesion 31 in the medical image 30 acquired in S1. In this case, the user can appropriately grasp the process in which the state of the lesion 31 changes. When acquiring the image during transition in S20 and S21, the CPU 23 may sequentially switch the plurality of predicted disease images 60 along the time series (for example, in a moving image) and display the plurality of predicted disease images on the display device 28. In this case, the medical image 30 acquired in S1 may be displayed before the plurality of predicted disease images 60. In addition, the CPU 23 may cause the display device 28 to simultaneously display a plurality of predicted disease images 60 side by side.

When an instruction to end the medical image processing is not input (S23: NO), the process returns to S11, and the processing in S11 to S23 is repeated. When an end instruction is input (S23: YES), the medical image processing ends.

The technique disclosed in the above embodiment is merely an example. Accordingly, it is also possible to change the technique exemplified in the above embodiment. First of all, it is also possible to execute only some of the plurality of techniques exemplified in the above embodiments. For example, at least one of the processes in S11, S13, S15, and S17 may be omitted.

In S20 and S21 in the above embodiment, the predicted disease image 60 is acquired on the basis of the lesion removed image 40 generated from the medical image 30 acquired in S1 and the lesion information 73 added or changed according to the designated information from the user. That is, in the above embodiment, the predicted disease image 60 is acquired not on the basis of the medical image 30 itself but on the basis of the lesion removed image 40 acquired from the medical image 30. Therefore, in S1, the lesion removed image 40 (fundus vascular image in the present embodiment) may be acquired as a medical image of the subject used to acquire the predicted disease image 60. In this case, the processing in S2 may be omitted.

In the above embodiment, the predicted disease image generation model 74 (see FIG. 2) outputs the predicted disease image 74 by inputting the lesion removed image 40 acquired from the medical image 30 and the lesion information 73. However, it is also possible to change a specific method for acquiring the predicted disease image 60 on the basis of the medical image 30 and the lesion information 73. For example, the CPU 23 may extract an image of a region of the lesion 31 from the medical image 30. The CPU 23 may convert at least the position, range, type, color, or the like of the image of the region of the lesion 31 according to the lesion information 73 designated by the user. The CPU 23 may generate the predicted disease image 60 by combining the converted image with the medical image 30. The above processing may be executed by using a machine learning algorithm or may be executed by known image processing. In this case, the process of acquiring the lesion removed image 40 may be omitted.

Furthermore, in a case in which the medical image 30 is a fundus front image, the pre-modification image may be a map image that two-dimensionally shows a distribution (for example, the distribution of the thicknesses of at least one of the layers in the eye fundus) related to the structure of the fundus. In this case, the user may designate at least the position or the region of the lesion 31 by designating a region (for example, a region where the thickness of the layer is within a specific range) of a desired structure illustrated in the map image.

In addition, the CPU 23 may receive an instruction to designate the degree of disease (progress status or cure status) of the lesion 31 to be modified. When the degree of disease is designated, the CPU 23 may acquire the predicted disease image 60 obtained by modifying the color of the lesion 31 to a color (including color density, color distribution roughness, and the like) corresponding to the designated degree of disease on the basis of the medical image 30. In this case, the predicted disease image generation model 74 may be trained using the lesion information 73 including information of the degree of disease as training data for input. In this case, the lesion 31 whose color is converted according to the degree of disease is also appropriately displayed on the predicted disease image 60.

Note that the process of acquiring the medical image 30 in S1 in FIG. 4 is an example of the "image acquisition step". The process of displaying the pre-modification image 50 in S3 in FIG. 4 is an example of the "pre-modification image display step". The process of receiving the designation instruction related to the lesion 31 in S11, S13, S15, and S17 in FIG. 4 is an example of the "lesion reception step". The process of acquiring the predicted disease image 60 in S20 and S21 in FIG. 4 is an example of the "predicted disease image acquisition step". The process of displaying the predicted disease image in S21 in FIG. 4 is an example of the "predicted disease image display step". The process of acquiring the detection result regarding the lesion 31 in the medical image 30 in S4 to S7 in FIG. 4 is an example of the "lesion position acquisition step", the "lesion range acquisition step", and the "lesion type acquisition step".

LIST OF REFERENCE SIGNS

21 medical image processing device
23 CPU
24 storage device
28 display device
30 medical image
31 lesion
40 lesion removed image
50 pre-modification image
60 predicted disease image
73 lesion information
74 predicted disease image generation model

The invention claimed is:

1. A medical image processing device comprising:
a controller configured to execute:
an image acquisition step of acquiring a medical image of a tissue of a subject,
a pre-modification image display step of displaying, on a display, pre-modification image in which at least one of a position and a range of a lesion to be modified on the medical image is displayed,
a lesion reception step of receiving an instruction to designate at least one of a position and a range of the lesion to be modified in a state in which the pre-modification image is displayed on the display,
a predicted disease image acquisition step of, in a case in which at least one of a position and a range of the lesion is designated, acquiring a predicted disease image in which the lesion is modified according to designated information on the basis of the medical image acquired in the image acquisition step,
a predicted disease image display step of displaying the acquired predicted disease image and the pre-modification image on the display simultaneously or in a switching manner, and
acquiring the predicted disease image by inputting the image of the tissue of the subject and information of the lesion to a mathematical model trained by a machine learning algorithm in the predicted disease image acquisition step, such that the predicted disease image is output from the mathematical model, wherein the predicted disease image output from the mathematical model represents a future predicted state of the tissue of the subject.

2. The medical image processing device according to claim 1, wherein the controller further executes a lesion position acquisition step of acquiring a detection result of a position of a lesion in the medical image in a case in which the lesion already exists in the medical image acquired in the image acquisition step, and executes, in the lesion reception step and the predicted disease image acquisition step, processing of receiving the instruction and processing of acquiring the predicted disease image using the position of the lesion acquired in the lesion position acquisition step as the position of the already existing lesion.

3. The medical image processing device according to claim 1, wherein the controller further executes a lesion range acquisition step of acquiring a detection result of a range of a lesion in the medical image in a case in which the lesion already exists in the medical image acquired in the image acquisition step and executes, in the lesion reception step and the predicted disease image acquisition step, processing of receiving the instruction and processing of acquiring the predicted disease image using the range of the lesion acquired in the lesion range acquisition step as the range of the already existing lesion.

4. The medical image processing device according to claim 1, wherein the controller is capable of receiving an instruction to designate a type of the lesion to be modified in the lesion reception step and acquires, when the type of the lesion is designated, the predicted disease image with the lesion of the designated type being modified on the basis of the medical image in the predicted disease image acquisition step.

5. The medical image processing device according to claim 1, wherein the controller further executes a lesion type acquisition step of acquiring a detection result of a type of the already existing lesion in a case in which the lesion already exists in the medical image acquired in the image acquisition step and executes, when the type of the lesion is acquired in the lesion type acquisition step, processing of receiving the instruction and processing of acquiring the predicted disease image using the type of the lesion acquired as the type of the already existing lesion in the lesion reception step and the predicted disease image acquisition step.

6. The medical image processing device according to claim 1, wherein the controller acquires, when the range of the lesion is designated, in the predicted disease image acquisition step, the predicted disease image in which the range of the lesion is between the designated range and the range of the lesion in the medical image acquired in the image acquisition step together with the predicted disease image in which the lesion in the designated range is modified.

7. The medical image processing device according to claim 1, wherein the controller acquires the predicted disease image including the image of the lesion predicted from information of the lesion on the basis of the information of the lesion including at least one of the position and the range and the image of the tissue of the subject in the predicted disease image acquisition step.

8. A storage device storing a medical image processing program executed by a medical image processing device, wherein
the medical image processing program is executed by a controller of the medical image processing device to execute:
an image acquisition step of acquiring a medical image of a tissue of a subject,
a pre-modification image display step of displaying, on a display, a pre-modification image in which at least one of a position and a range of a lesion to be modified on the medical image is displayed,
a lesion reception step of receiving an instruction to designate at least one of a position and a range of the lesion to be modified in a state in which the pre-modification image is displayed on the display,
a predicted disease image acquisition step of, in a case in which at least one of a position and a range of the lesion is designated, acquiring a predicted disease image in which the lesion is modified according to designated information on the basis of the medical image acquired in the image acquisition step,
a predicted disease image display step of displaying the acquired predicted disease image and the pre-modification image on the display simultaneously or in a switching manner, and
acquiring the predicted disease image by inputting the image of the tissue of the subject and information of the lesion to a mathematical model trained by a machine learning algorithm in the predicted disease image acquisition step, such that the predicted disease image is output from the mathematical model, wherein the predicted disease image output from the mathematical model represents a future predicted state of the tissue of the subject.

9. A medical image processing method comprising:
an image acquisition step of acquiring a medical image of a tissue of a subject,
a pre-modification image display step of displaying, on a display, pre-modification image in which at least one of a position and a range of a lesion to be modified on the medical image is displayed,
a lesion reception step of receiving an instruction to designate at least one of a position and a range of the lesion to be modified in a state in which the pre-modification image is displayed on the display,
a predicted disease image acquisition step of, in a case in which at least one of a position and a range of the lesion is designated, acquiring a predicted disease image in which the lesion is modified according to designated information on the basis of the medical image acquired in the image acquisition step,
a predicted disease image display step of displaying the acquired predicted disease image and the pre-modification image on the display simultaneously or in a switching manner, and
acquiring the predicted disease image by inputting the image of the tissue of the subject and information of the lesion to a mathematical model trained by a machine learning algorithm in the predicted disease image acquisition step, such that the predicted disease image is output from the mathematical model, wherein the predicted disease image output from the mathematical model represents a future predicted state of the tissue of the subject.

\* \* \* \* \*